United States Patent [19]

Tanihara et al.

[11] Patent Number: 4,925,787
[45] Date of Patent: May 15, 1990

[54] MONOCLONAL ANTI-IDIOTYPIC ANTIBODY, METHOD FOR PRODUCTION THEREOF, AND HYBRIDOMA PRODUCING SAID ANTIBODY

[75] Inventors: Masao Tanihara; Hideaki Yamada, both of Kurashiki; Toshihide Nakashima, Toyonaka; Yoshiaki Omura, Okayama; Koichi Takakura, Nishinomiya, all of Japan

[73] Assignees: Agency of Industrial Science and Technology; Ministry of International Trade and Industry, both of Tokyo, Japan

[21] Appl. No.: 175,303

[22] Filed: Mar. 30, 1988

[30] Foreign Application Priority Data

Sep. 8, 1987 [JP] Japan .................... 62-223173

[51] Int. Cl.$^5$ ............... G01N 33/577; G01N 33/535
[52] U.S. Cl. ........................ 435/7; 436/529; 436/535; 436/548; 530/387; 530/413; 530/402; 530/813; 530/808; 530/809; 435/240.27; 935/103; 935/108; 935/110
[58] Field of Search ............. 436/548, 528–530; 435/172.2, 240.27, 68; 530/387; 424/85

[56] References Cited

U.S. PATENT DOCUMENTS

4,536,479   8/1985   Vander-Mallie .................... 436/537

FOREIGN PATENT DOCUMENTS

WO86/01539   3/1986   PCT Int'l Appl.

OTHER PUBLICATIONS

Lefvert, A. et al., Eur. J. Immunol, 12(9), 790–792, (Sep. 1982)
Mehraban, F. et al., Eur. J. Biochem., 138(1), 53–61, (Jan. 1984).
*Nature*, (1983), vol. 301, pp. 611–614, "Naturally Occurring Anti-Idiotypic Antibodies in Myasthenia Gravis Patients", Dwyer et al.
*Eur. J. Immunol.*, (1982), vol. 12, pp. 790–792, "A Monoclonal Anti-Idiotypic Antibody Against Anti--Receptor Antibodies From Myasthenic Sera", Lefvert et al.

*Primary Examiner*—Christine M. Nucker
*Attorney, Agent, or Firm*—Oblon, Spivak, McClelland, Maier & Neustadt

[57] ABSTRACT

A monoclonal anti-idiotypic antibody specific to a human IgG$_1$ type monoclonal antibody possessing specificity to nicotinic acetylcholine receptor; a method for the production of the aforementioned monoclonal anti-idiotypic antibody by the steps of immunizing an animal with a human IgG$_1$ type monoclonal antibody specific to nicotinic acetylcholine receptor, collecting antibody-producing cells from the animal, fusing the collected cells with neoplastic cells, selecting from the product of fusion a hybridoma capable of producing a monoclonal anti-idiotypic antibody specific to the human IgG$_1$ type monoclonal antibody possessing specificity to nicotinic acetylcholine receptor, propagating the selected hybridoma thereby giving rise to said monoclonal anti-idiotypic antibody, and collecting the produced monoclonal anti-idiotypic antibody; and use of the monoclonal anti-idiotypic antibody as a reagent and as an adsorbent.

17 Claims, 8 Drawing Sheets

FIG.3 (1)     FIG.3 (2)
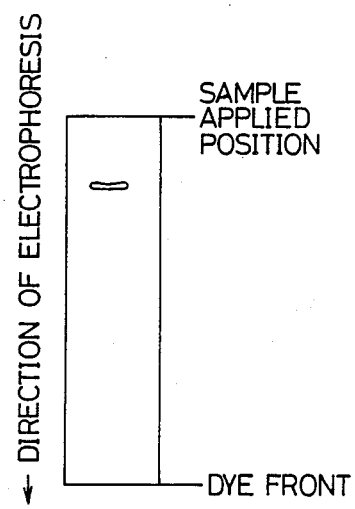 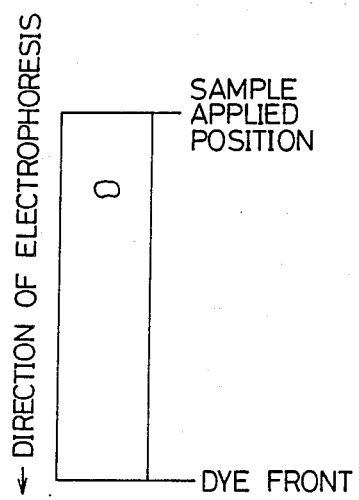

MONOCLONAL ANTI-IDIOTYPIC ANTIBODY, METHOD FOR PRODUCTION THEREOF, AND HYBRIDOMA PRODUCING SAID ANTIBODY

BACKGROUND OF THE INVENTION

1. Field of the Invention

This invention relates to a monoclonal anti-idiotypic antibody, a hybridoma producing the antibody, and use thereof.

The monoclonal anti-idiotypic antibody which is provided by the present invention is specific to the human $IgG_1$ type monoclonal antibody specific to nicotinic acetylcholine receptor. It is, therefore, useful in the diagnosis and treatment of myasthenia gravis which is characterized mainly by impairment of neuromuscular transmission caused by the presence of autoantibodies against the nicotinic acetylcholine receptor present on the post-synaptic membrane of the neuromuscular junction.

2. Prior Art Statement

It is reported in European Journal of Immunology, Vol. 12, pages 790–792 (1982) that one of the hybridoma strains acquired by immunizing a BALB/c mouse with the heavy chain part of an antigen-binding fragment (Fab) originating in the $IgG_3$ of the serum from a patient of myasthenia gravis, fusing the spleen cells collected from the immunized BALB/c mouse with a cell line SP2/0-Ag14 of B lymphocytoma thereby producing a hybridoma, and then cloning the hydridoma is capable of yielding a monoclonal anti-idiotypic antibody to the antibody against the nicotinic acetylcholine receptor originating in the patient of myasthenia gravis. In Nature, Vol. 301, pages 611–614 (1983), it is reported that the cell line obtained by fusing the peripheral blood lymphocyte of a patient of myasthenia gravis with the variant, GK-5, of B cell produce a human monoclonal antibody possessing a $\mu$ chain as a heavy chain and a $\kappa$ chain as a light chain and that the human monoclonal antibody produced by the cell line is presumed to be an anti-idiotypic antibody against the antibody to the nicotinic acetylcholine receptor. Japanese Patent Public Disclosure SHO 56(1981)-128722 states that an antibody against the antibody to the acetylcholine receptor was obtained by immunizing a rabbit with an antibody against the acetylcholine receptor obtained from the serum of a patient of myasthenia gravis, isolating an immunoglobulin by fractionation from the antiserum taken from the immunized rabbit, and subjecting the immunoglobulin to affinity chromatography using a Sepharose having immobilized thereon an antibody to the acetylcholine receptor. It also discloses a method for the removal of an antibody against the acetylcholine receptor, which method comprises preparing a material for removal of an antibody against the acetylcholine receptor by immobilizing on an organic or inorganic carrier an antibody to the aforementioned antibody against the acetylcholine receptor and causing this material to contact a body fluid containing an antibody against the acetylcholine receptor.

The method reported in European Journal of Immunology can be hardly called a practical approach inasmuch as the autoantibody against the nicotinic acetylcholine receptor is present only in a very minute amount in the $IgG_3$ which gives rise to the heavy chain part of the antigen-binding fragment. The method which is reported in Nature is not a practical approach either since the lymphocyte capable of producing an anti-idiotypic antibody to the antibody against the nicotinic acetylcholine receptor is present only in a trace amount in the peripheral blood lymphocyte of a patient of myasthenia gravis. The method which is disclosed in Japanese Patent Public Disclosure SHO 56(1981)-128722 cannot be called practical because the antibody against the acetylcholine receptor is present only in a very minute amount in the serum of a patient of myasthenia gravis and further because the antibody to the antibody against the acetylcholine receptor is present only in a negligibly small amount in the antiserum obtained by immunizing a rabbit with an antibody against the acetycholine receptor. Further, the material for the removal of the antibody against the acetycholine receptor does not easily acquire uniform quality because the antibody to the antibody against the acetylcholine receptor to be contained in the removing material varies in nature depending on particular rabbit immunized with the antibody.

OBJECT AND SUMMARY OF THE INVENTION

One object of the present invention is to provide a novel monoclonal anti-idiotypic antibody which exhibits specificity to a human $IgG_1$ type monoclonal antibody specific to nicotinic acetylcholine receptor. Another object of this invention is to provide a method for efficient production of the novel monoclonal anti-idiotypic antibody. A further object of this invention is to provide a novel hybridoma which is capable of producing efficiently the novel monoclonal anti-idiotypic antibody. Yet another object of this invention is to provide a use of the novel monoclonal anti-idiotypic antibody.

To accomplish the objects described above, this invention provides a monoclonal anti-idiotypic antibody which is specific to a human $IgG_1$ type monoclonal antibody specific to nicotinic acetylcholine receptor (hereinafter the term "nicotinic acetycholine receptor" will be abbreviated as "AChR" and the term "human $IgG_1$ type monoclonal antibody specific to nicotinic acetylcholine receptor" referred to as "human $IgG_1$ type monoclonal anti-AChR antibody"), a method for the production of a monoclonal anti-idiotypic antibody specific to a human $IgG_1$ type monoclonal anti-AChR antibody, characterized by immunizing an animal with a human $IgG_1$ type monoclonal anti-AChR antibody, fusing antibody-producing cells collected from the animal with neoplastic cells, selecting from the product of fusion a hybridoma capable of producing a monoclonal anti-idiotypic antibody specific to the human $IgG_1$ type monoclonal anti-AChR antibody, causing propagation of the hybridoma thereby giving rise to the aforementioned monoclonal anti-idiotypic antibody, and separating the monoclonal anti-idiotypic antibody, and a hybridoma capable of producing the monoclonal anti-idiotypic antibody.

This invention is further directed to detection, removal, and adsorption of an antibody against AChR by the use of the monoclonal anti-idiotypic antibody which is specific to the aforementioned human $IgG_1$ type monoclonal anti-AChR antibody.

The above and other objects and features of the invention will become more apparent from the following detailed description with reference to the accompanying drawings.

BRIEF DESCRIPTION OF THE DRAWINGS

FIG. 3 (1) shows the electrophoretic pattern of a human $IgG_1$ type monoclonal anti-AChR antibody obtained in Referential Example 1(6).

FIG. 3 (2) shows the electrophoretic pattern of a commercially available human IgG.

DETAILED DESCRIPTION OF THE PREFERRED EMBODIMENTS

Figure 1:
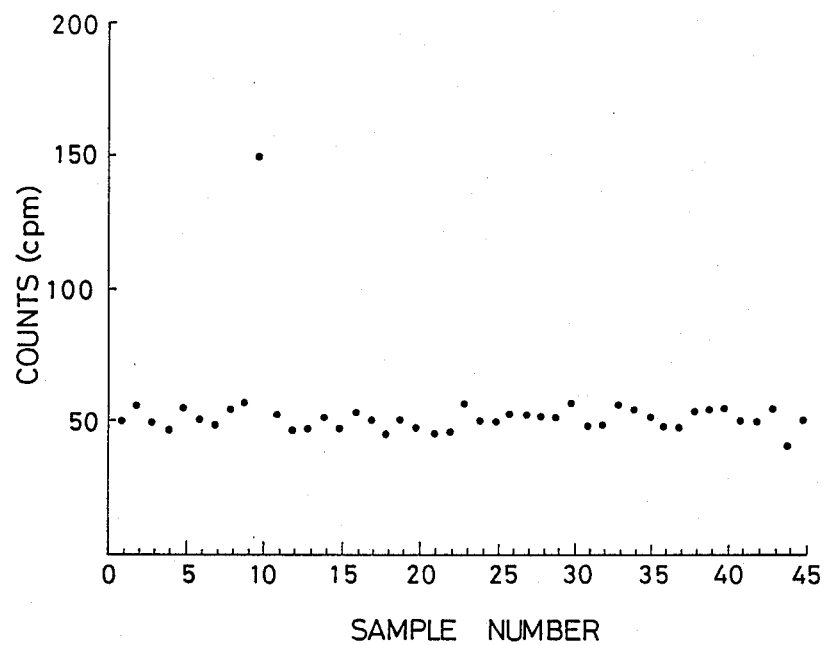
FIG. 1 shows the data on radioactivity obtained in Referential Example 1 (4), for the precipitates (Sample Nos. 1 to 44) formed when the culture supernatants of 44 of the total of 49 hybridomas producing human antibodies were used and the precipitate (Sample No. 45) formed when the culture supernatant of the $G(Ag_1)_2$-cl 7B strain was used.

The hybridoma capable of producing the monoclonal anti-idiotypic antibody specific to the aforementioned human $IgG_1$ type monoclonal anti-AChR antibody is obtained by first immunizing an animal with a human $IgG_1$ type monoclonal anti-AChR antibody, fusing antibody-producing cells obtained from the animal with neoplastic cells, and then subjecting the product of fusion to the following procedure.

As cells producing an antibody against the human $IgG_1$ type monoclonal anti-AChR antibody, those lymphocytes which are present in the spleen or the lymph node of an animal immunized with the human $IgG_1$ type monoclonal anti-AChR antibody, for example, may be used. The immunization of the animal with the human $IgG_1$ type monoclonal anti-AChR antibody can be carried out by the conventional method which is normally employed for the immunization of an animal with an antigen. For example, the human $IgG_1$ type monoclonal anti-AChR antibody generally prepared in the form of a mixture with a phosphate buffered salt solution (hereinafter referred to as "PBS"), a salt solution such as a physiological saline solution, and adjuvants such as Freund's complete adjuvant and aluminum hydroxide is administered at least twice intraperitoneally, hypodermically, or intramuscularly to a given animal. About three days after the final administration, the antibody-producing cells are collected from the animal. As examples of animals which can be used effectively for this immunization, there can be cited rodents, typically by mice and rats, lagomorphs, typically rabbits and hares, and ruminants, typically sheep. The antibody-producing cells and the neoplastic cells which are to be subjected to cell fusion are desired to originate in animals of one and the same species. Among the animals mentioned, it is desirable to use rodents because they are readily available and are well known to produce numerous types of neoplastic cells. It is particularly desirable to use BALB/c mice.

The type of neoplastic cells is not particularly limited except that they should be capable of imparting a hyperplastic capacity to cells capable of producing a monoclonal anti-idiotypic antibody specific to the human $IgG_1$ type monoclonal anti-AChR antibody. From the standpoint of the efficiency of fusion with antibody-producing cells and the cloning efficiency of the produced hybridoma, stability, hyperplastic capacity, and antibody-producing capacity, it is desirable to use myeloma cell lines originating in an animal of the same species as the animal from which the antibody-producing cells were collected or a hybridoma derived from the myeloma cell lines. After the fusion of the cells, for the purpose of facilitating the subsequent separation between the produced hybridoma capable of producing a monoclonal anti-idiotypic antibody specific to the human $IgG_1$ type monoclonal anti-AChR antibody and the used neoplastic cells, it is desirable to use as the neoplastic cells those 6-thioguanine-resistant cells, 8-azaguanine-resistant cells, or 5-bromodeoxyuridine-resistant cells which are sensitive to hypoxanthine-aminopterin-thymidine. As concrete examples of such neoplastic cells, there can be cited myeloma cell strains originating in BALB/c mice such as $P_3$-NSI/1-$Ag_4$-1 strain [ATCC No. $T_1B_{18}$; European Journal of Immunology, Vol. 6, page 511 (1976)], $P_3$-X63-$Ag_8$ strain [ATCC No. $T_1B_9$; Nature, Vol. 256, page 495 (1975)], $P_3$-X63-$Ag_{8.653}$ strain [ATCC No. CRL 1580; Journal of Immunology, Vol. 123, page 1548 (1979)], S194/5. XXO. BU.1 strain [ATCC No. $T_1B_{20}$; Journal of Experimental Medicine, Vol. 148, page 313 (1978)], and MPC-11 strain [ATCC No. CCL 167; Journal of Experimental Medicine, Vol. 131, page 515 (1970)]; myeloma cell strains originating in rats such as Y3-Ag 1.2.3. strain [ATCC No. CRL 1631; Nature, Vol. 277, page 131 (1979)]; and hybridoma strains as descendants from myeloma cell strains originating in BALB/c mice such as SP2/0-$Ag_{14}$ strain [ATCC No. CRT 1581; Nature, Vol. 276, page 269 (1978)]. Among the strains enumerated above, it is particularly desirable to use the $P_3$-NSI/1-$Ag_4$-1 strain.

The fusion of the antibody-producing cells and the neoplastic cells is carried out in a buffered solution generally in the presence of a fusing agent in accordance with the conventional method popularly employed for cell fusion. In the fusion, the antibody-producing cells and the neoplastic cells are used in proportions such that their ratio in cell number generally falls in the range of about 10:1 to about 1:1, preferably about 4:1 to about 1.5:1. As the fusing agent, polyethylene glycol, Sendai virus (Hemagglutinating Virus of Japan), etc. may be used. From the standpoint of ease of handling and efficiency of fusion, it is desirable to use polyethylene glycol possessing an average molecular weight approximately in the range of 1,000 to 5,000. Properly, this polyethylene glycol is used in such an amount that the concentration thereof in the buffered solution will fall approximately in the range of 40 to 60% by weight. The fusion of cells is generally carried out by adding the antibody-producing cells and the neoplastic cells to an animal cell culture medium or a balanced salt solution and stirring the culture medium or salt solution with the fusing agent added thereto at a temperature of about 37° C. for a period of about 2 minutes, for example. Examples of the animal cell culture medium include RPMI- 1640 medium, Hanks' minimum essential medium, and Eagle's minimum essential medium. Examples of the balanced salt solution include Hanks' balanced salts solution and Earle's balanced salts solution. Otherwise, the fusion of the antibody-producing cells and the neoplastic cells may be carried out by the method of electric fusion.

After the process of fusion described above is completed, the hybridoma capable of producing a monoclonal anti-idiotypic antibody specific to the human $IgG_1$ type monoclonal anti-AChR antibody is selected from the cell mixture produced by the fusion as follows. First, from the cell mixture, the hybridoma of the antibody-producing cells and the neoplastic cells is selected. When cells sensitive to hypoxanthine-aminopterin-thymidine have been used as neoplastic cells, the hybridoma of the antibody-producing cells and the neoplastic cells can be selectively propagated by culturing the cell mixture resulting from the cell fusion in a culture medium containing hypoxanthine, aminopterin, and thymidine (hereinafter the medium will be referred to as "HAT culture medium"). The culture in the HAT culture medium yields highly desirable results when the concentration of the cell mixture in the culture medium is adjusted to generally in the range of $1 \times 10^6$ to $1 \times 10^7$ cells/ml. The HAT culture medium is prepared, for example, by adding to such an animal cell culture medium as RPMI-1640 medium such an amount of fetal bovine blood serum as to register a concentration approximately in the range of 10 to 15% by volume and further adding thereto hypoxanthine, aminopterin, and thymidine. The concentrations of hypoxanthine, aminopterin, and thymidine in the HAT culture medium are not particularly limited but not be such that the compounds contained should exert an adverse effect on the growth of the hybridoma aimed at. Generally, it is desirable to adjust their concentrations to approximately $1 \times 10^{-4}$ mol/liter, $4 \times 10^{-7}$ mol/liter, and $1.6 \times 10^{-5}$ mol/liter respectively. The culture in the HAT culture medium is carried out in a stationary state in air containing about 5 to 8% of carbon dioxide at a temperature of about 37° C. for a period of about one to four weeks. Then, from the hybridoma which has been selected from the cell mixture, a hybridoma capable of producing an antibody specific to the human $IgG_1$ type monoclonal anti-AChR antibody is separated. The question as to whether the hybridoma is capable of producing an antibody specific to the human $IgG_1$ type monoclonal anti-AChR antibody or not can be determined by the method of enzyme linked immunosorbent assay (hereinafter referred to as the "ELISA" method) or the radioimmunoassay method (hereinafter referred to as the "RIA" method), for example. By subjecting the hybridoma isolated as described above to cloning by the limiting dilution method, for example, there can be obtained a propagable hybridoma strain capable of producing a monoclonal anti-idiotypic antibody specific to the human $IgG_1$ type monoclonal anti-AChR antibody. As concrete examples of the hybridoma strain of the foregoing description, there can be cited TA-1 strain deposited with the Fermentation Research Institute, Agency of Industrial Science & Technology on March 15, 1988 and assigned the deposit number FERM BP-1793 under the Budapest Treaty, TA-2 strain deposited with the Fermentation Research Institute, Agency of Industrial Science & Technology on March 15, 1988 and assigned the deposit number FERM BP-1794 under the Budapest Treaty, TA-3 strain deposited with the Fermentation Research Institute, Agency of Industrial Science & Technology on March 15, 1988 and assigned the deposit number FERM BP-1795 under the Budapest Treaty, and TA-5 strain deposited with the Fermentation Research Institute, Agency of Industrial Science & Technology on March 15, 1988 and assigned the deposit number FERM BP-1796 under the Budapest Treaty. The TA-1 strain, TA-2 strain, TA-3 strain, and TA-5 strain have been screened from the hybridoma obtained by the fusion of the P3-NSI/1-AG$_4$-1 strain with the lymphocytes present in the spleen of a BALB/c mouse immunized with a human $IgG_1$ type monoclonal antibody which is specific to AChR and possesses a molecular weight of $180,000 \pm 20,000$ as determined by the method of polyacrylamide gel electrophoresis carried out in the presence of sodium dodecyl sulfate.

When the hybridoma strain which has been obtained as described above is cultured at a temperature of about 37° C. in a culture medium prepared by adding fetal bovine serum in an amount calculated to register a final concentration approximately in the range of 10 to 15% by volume to an animal cell culture medium such as, for example, the RPMI-1640 medium in air containing about 5 to 8% of carbon dioxide, the hybridoma strain gradually propagates to give rise to a monoclonal anti-idiotypic antibody specific, in vitro, to the human $IgG_1$ type monoclonal anti-AChR antibody. When the hybridoma strain is transplanted to the body of an animal of the same species as the animal used for obtaining the neoplastic cells to be used in the cell fusion, the hybridoma strain propagates as the animal is raised, in vivo to give birth to a monoclonal anti-idiotypic antibody specific to the human $IgG_1$ type monoclonal anti-AChR antibody.

The monoclonal anti-idiotypic antibody specific to the human $IgG_1$ type monoclonal anti-AChR antibody is purified from the culture supernatant of hybridoma or from the body fluid such as the abdominal dropsy or serum of the animal used for the transplantation of the hybridoma. The separation in an isolated form of the target monoclonal anti-idiotypic antibody from the culture supernatant or from the body fluid mentioned above is accomplished by subjecting the supernatant or the body fluid to such a treatment as salting out using a salt such as ammonium sulfate, ultrafiltration, gel permeation chromatography, affinity chromatography, or ion-exchange chromatography, for example.

The present invention further embraces a reagent for the detection of an antibody against the AChR containing the monoclonal anti-idiotypic antibody specific to the human $IgG_1$ type monoclonal anti-AChR antibody (hereinafter the antibody against AChR will be referred to as "anti-AChR antibody") a method for the removal of the anti-AChR antibody characterized by causing the aforementioned monoclonal anti-idiotypic antibody to contact the anti-AChR antibody, and an adsorbent for the removal of the anti-AChR antibody formed by immobilizing the aforementioned monoclonal anti-idiotypic antibody on a carrier.

The anti-AChR antibody present in a sample such as blood serum can be qualitatively or quantitatively detected by using the reagent for detection of the anti-AChR antibody containing a monoclonal anti-idiotypic antibody specific to the human $IgG_1$ type monoclonal anti-AChR antibody in a method such as the ELISA method, the RIA method, the fluorescent immuno measuring method, or the hemagglutination method which effects detection of an antigen by the antigen-antibody reaction. The aforementioned monoclonal anti-idiotypic antibody to be used as the reagent for detection of the anti-AChR antibody may be in a form bearing a radioactive label, an enzymatic label, a biotin label, or a fluorescent label.

The removal of the anti-AChR antibody by the use of the monoclonal anti-idiotypic antibody specific to the human $IgG_1$ type monoclonal anti-AChR antibody is effected, for example, by causing the absorbent for removal of the anti-AChR antibody formed by immobilizing the monoclonal anti-idiotypic antibody on a carrier to contact a body fluid containing the anti-AChR antibody thereby effecting adsorption of the anti-AChR antibody on the adsorbent. The carrier to be used for the immobilization of the monoclonal anti-idiotypic antibody can be any of the conventional carriers which are insoluble in body fluids and are generally employed for the immobilization of an antibody. The carrier to be used is desired to posses such a reactive functional group as amino group or carboxyl group which is available for the formation of a covalent bond with the antibody and to possess a hydrophilic surface. The carrier can be used in any desired form such as particles, fibers, sheet, or hollow fibers. As concrete examples of the carrier usable effectively for the immobilization, there can be cited organic carriers including cellulose type carriers such as Cellulofine GCL-20000C (marketed by SEIKAGAKU KOGYO CO., LTD.); polyacrylamide type carriers such as Trisacryl GF2000 (product of L. K. B. Produkter, Sweden); polyvinyl alcohol type carriers such as TSK gel Toyopearl HW-75C (product of Toyo Soda Manufacturing Co., Ltd.); and Agarose type carriers such as CNBr-Sepharose CL4B (product of Pharmacia, Sweden) and inorganic carriers including porous glass. Otherwise, a carrier which is produced by coating the surface of a substrate such as porous glass with a copolymer obtained by copolymerizing a hydrophilic acrylate or methacrylate type monomer such as hydroxyethyl acrylate or hydroxyethyl methacrylate with acrylic acid, methacrylic acid, an aminoalkyl acrylate such as aminoethyl acrylate, or an aminoalkyl methacrylate such as aminoethyl methacrylate (Japanese Patent Publication SHO 61(1986)-59175). The immobilization of the monoclonal anti-idiotypic antibody on the carrier is carried out by any of the conventional methods generally employed in immobilizing an antibody on a carrier. For example, the method which effects the immobilization by cross-linking the amino group of the monoclonal anti-idiotypic antibody and the amino group of the carrier through the medium of glutaldehyde and the method which accomplishes the immobilization by converting the carboxyl group of the carrier into a succinimido-oxycarbonyl group by reaction with N-hydroxysuccinimide and causing the amino group of the monoclonal anti-idiotypic antibody to react with the succinimido-oxycarbonyl group can be cited. When the monoclonal anti-idiotypic antibody is introduced into the blood vessel of a patient of myasthenia gravis who retains an anti-AChR antibody in his system, the monoclonal anti-idiotypic antibody and the anti-AChR antibody react and form an immune complex and then the immune complex is decomposed by the reticular cells. By the injection of the monoclonal anti-idiotypic antibody into the blood vessel of the patient, therefore, the anti-AChR antibody can be removed from the patient's body.

The human $IgG_1$ type monoclonal anti-AChR antibody to be used as an immunogen for an animal in the production of the monoclonal anti-idiotypic antibody of this invention specific to the human $IgG_1$ type monoclonal anti-AChR antibody can be produced, for example, by subjecting human cells capable of producing an anti-AChR antibody (hereinafter the cells will be referred to as "anti-AChR antibody-producing human cells") to cell fusion with such human neoplastic cells as propagable human lymphoblastoid cell lines or human myeloma cell lines; to transformation by infection with such a virus as Epstein-Barr virus; or to protracted culture in the presence of such a cell-propagating factor as Interleukin 2 (IL-2), Interleukin 4 (IL-4), Interleukin 5 (IL-5), B cell-stimulating factor (BSF-1), or B cell-stimulating factor 2 (BSF-2) thereby effecting separation of propagable cells capable of producing a human $IgG_1$ type monoclonal anti-AChR antibody, culturing the separated propagable cells thereby producing a human $IgG_1$ type monoclonal anti-AChR antibody, and collecting the human $IgG_1$ type monoclonal anti-AChR antibody. As the aforementioned anti-AChR antibody-producing human cells, those lymphocytes which are taken from the thymus gland, the spleen, the lymph node, and the peripheral blood of a patient of autoimmunity such as myasthenia gravis retaining an anti-AChR antibody as an autoantibody in the body can be cited. Since the anti-AChR antibody-producing human cells occur in relatively large amounts at a high concentration in the thymus and the spleen of a patient of myasthenia gravis, it is practical to utilize as the anti-AChR antibody-producing human cells those lymphocytes which are present in the thymus and the spleen of a patient of myasthenia gravis. As the human $IgG_1$ type monoclonal anti-AChR antibody to be used for the aforementioned cell fusion, it is proper, from the standpoint of facilitating the separation of these cells from the hybridoma capable of producing a human $IgG_1$ type monoclonal anti-AChR antibody subsequently to the cell fusion, to employ 6-thioguanine-resistant cells, 8-azaguanine-resistant cells, or 5-bromodeoxyuridine-resistant cells which are sensitive to hypoxanthine, aminopterin, and thymidine. The propagable human lymphoblastoid cells can be produced, for example, by infecting human lymphocytes with such a virus as Epstein-Barr virus thereby transforming the human lymphocytes. As concrete examples of propagable human lymphoblastoid cells sensitive to hypoxanthine, aminopterin, and thymidine, there can be cited $G(Ag_1)_2$-cl 7B strain deposited with the Fermentation Research Institute, Agency of Industrial Science & Technology on March 15, 1988 and assigned the deposit number FERM BP-1797 under the Budapest Treaty, and GM4672 strain [Journal of Experimental Medicine, Vol. 158, pages 718–730 (1983)]; H35.1.1,0467.3 strain [Journal of Experimental Medicine, Vol. 156, pages 930–935 (1982)]; KR-4 strain (Proceedings of the National Academy of Sciences of the United States of America, Vol. 79, pages 6651–6655 (1982)]; RH-L4 strain [Journal of Immunological Methods, Vol. 61, pages 17–32 (1983)]; GM1500 6TG-A12 strain [Nature, Vol. 288, pages 488–489 (1980)]; WI-L2-729HF$_2$ strain [Journal of Immunology, Vol. 132, pages 1798–1803 (1984)]; and LICR-LON-HMy-2 strain ]Proceedings of the National Academy of Sciences of the United States of America, Vol. 80, pages 2026–2030 (1983)].

The $G(Ag_1)_2$-cl 7B strain is obtained by transforming peripheral blood lymphocytes of a patient of rheumatoid arthritis with Epstein-Barr virus and imparting 8-azaguanine resistance to the transformed cell. The G(Ag$_1$)$_2$-cl 7B strain also possesses resistance to ouabain. As concrete examples of the human myeloma cell lines sensitive to hypoxanthine, aminopterin, and thymidine, there can be cited U-266 AR$_1$ strain [Proceeding of the National Academy of Sciences of the United States of America, Vol. 77, pages 5429–5431 (1980)] and RPMI 8226 strain [ATCC No. CCL 155; Journal of Immunology, Vol. 131, pages 1201–1204 (1983)]. The propagable human cells capable of producing a human IgG$_1$ type monoclonal anti-AChR antibody are obtained by the method of effecting cell fusion between anti-AChR antibody-producing human cells and propagable human lymphoblastoid cells. From the standpoint of acquiring the cells with high efficiency and ensuring high antibody-producing capacity and propagating capacity, it is particularly desirable to obtain the propagable human cells by the cell fusion between the anti-AChR antibody-producing human cells and the G(Ag$_1$)$_2$-cl 7B strain. The acquisition of propagable cells capable of producing a human IgG$_1$ type monoclonal anti-AChR antibody by the cell fusion of anti-AChR antibody-producing human cells and propagable human lymphoblastoid cells and the acquisition of the human IgG$_1$ type monoclonal anti-AChR antibody by the culture of the aforementioned cells are attained by the same methods as employed respectively for the acquisition of the hybridoma capable of producing the monoclonal anti-idiotypic antibody specific to the human IgG$_1$ type monoclonal anti-AChR antibody by the cell fusion between antibody-producing cells collected from an animal immunized with the aforementioned human IgG$_1$ type monoclonal anti-AChR antibody and neoplastic cells and the acquisition of a monoclonal anti-idiotypic antibody by the culture of the aforementioned hybridoma. As the propagable cells which are capable of producing the human cells which are obtained as described above, the T/G-59(5C) strain deposited with the Fermentation Research Institute, Agency of Industrial Science & Technology on March 15, 1988 and assigned the deposit number FERM BP-1798 under the Budapest Treaty, which is separated from the hybridoma obtained by the fusion of the G(Ag$_1$)$_2$-cl 7B strain with the lympocytes present in the thymus gland of a patient of myasthenia gravis can be cited, for example. As the human IgG$_1$ type monoclonal anti-AChR antibody to be obtained by culturing propagable cells possessing a capacity to produce a human IgG$_1$ type monoclonal anti-AChR antibody, the human IgG$_1$ type monoclonal anti-AChR antibody which is produced by the aforementioned T/G-59(5C) strain, possesses a molecular weight of 180,000±20,000, and is specific to the AChR can be cited, for example. This molecular weight is determined, for example, by the method of polyacrylamide gel electrophoresis which is carried out in the presence of sodium dodecyl sulfate as introduced in Nature, Vol. 227, pages 680–685 (1970). The electrophoresis according to this method is carried out in the absence of such a reducing agent as 2-mercapto-ethanol to precludes otherwise possible reductive decomposition of the human IgG$_1$ type monoclonal anti-AChR antibody.

Now, the present invention will be described more specifically below with reference to working examples. It should be noted, however, that this invention is not limited by the working examples.

REFERENTIAL EXAMPLE 1

First, the production of the IgG$_1$ type monoclonal anti-AChR antibody to be used in the present invention will be described below.

(1) Preparation of thymocytes

The thymocytes were obtained by excising the thymus from a patient of myasthenia gravis, washing the thymus with a Dulbecco's modified Eagle's medium, then pulverizing the washed thymus on a stainless steel mesh, collecting the cells which had passed the mesh, and centrifugally washing the cells three times with a RPMI-1640 medium.

(2) Fusion of cells

The thymocyte obtained in step (1) above in an amount of $1.04 \times 10^8$ cells and a G(Ag$_1$)$_2$-cl 7B strain in an amount of $5.2 \times 10^7$ cells were mixed with 1 ml of a mixed solution obtained by the combination of 1 g of polyethylene glycol possessing an average molecular weight of 1,500 and 1 ml of a RPMI-1640 medium and then stirred at a temperature of 37° C. for two minutes. By adding gradually 9 ml of a RPMI-1640 medium to the resultant mixture in a stirred state and then centrifuging the resultant mixture, a cell mixture was obtained in the form of a precipitate. A HAT culture medium was prepared by adding hypoxanthine, aminopterin, and thymidine and fetal bovine serum to a RPMI-1640 medium in amounts such as to register respective concentrations of $1 \times 10^{-4}$ mol/liter, $4 \times 10^{-7}$ mol/liter, $1.6 \times 10^{-5}$ mol/liter, and about 13% by volume. To the HAT culture medium, the aforementioned cell mixture was added in an amount such as to register a concentration of $2.5 \times 10^6$ cells/ml. The culture medium containing cells obtained as described above was dispensed in a unit volume of 0.1 ml into 575 wells of a microwell plate made of polystyrene (6 covered microwell plates each containing 96 wells; produced by Nunc Corp., Denmark) and cultured in a stationary state in the air containing 7% of carbon dioxide at a temperature of 37° C. After 10 to 20 days' culture, growth of hybridoma was recognized in 118 wells.

(3) Screening of hybridoma producing human antibody

In a phosphate buffered solution (PBS), an IgG fraction of goat antiserum against a human IgG (heavy and light chains) (produced by Miles-Yeda Corp., Israel) was dissolved in a concentration of 0.05 mg/ml. The resultant solution was dispensed in a unit volume of 50 μl into the wells of a microwell plate made of polyvinyl chloride (96-well plate; produced by Becton-Dickinson and Company, the U.S.A. and marketed under the tradename "Falcon 3912") and were left standing overnight at 4° C. to effect adsorption of antibody on the plate. The solution was removed from the individual wells. Then a PBS solution containing 5% by volume of fetal bovine serum was dispensed in a unit volume of 300 μl into the wells and then left standing at a temperature of 37° C. for two hours so as to effect blocking of the solid-phase surface which had not adsorbed antibody. The wells were washed with a PBS solution containing 5% by volume of fetal bovine serum. Then, the supernatant of the wells in which growth of hybridoma was recognized in the step (2) above was dispensed in a unit volume of 50 μl to the wells, left standing at 37° C. for one hour, and washed with a PBS solution containing 5% by volume of fetal bovine serum. Anti-human Ig antibody labeled with horseradish-peroxidase (Species - specific Whole Antibody, produced by Amersham & Company, England) was dissolved in a concentration of about 2 μg/ml in a PBS solution containing 5% by volume of fetal bovine serum. The resultant solution was dispensed in a unit volume of 50 μl to the wells and left standing at a temperature of 37° C. for one hour. The wells were washed with PBS. Then, a tris buffered solution (pH 7.4) containing 2,2'-azino-bis(3-ethylbenzothiazoline-6-sulfonic acid) in a concentration of 1 mmol/liter and also containing hydrogen peroxide in a concentration of 0.0045% by weight was dispensed in a unit volume of 100 μl into the wells and shaken at room temperature for 15 minutes to effect coloration. By testing the portions of solution in the individual wells for absorbance at wavelengths of 409 nm and 501 nm, it was found that a large difference of absorbance at the two wavelengths was present in the portions of solution in 49 of a total of 118 wells. From this result, it was concluded that the hybridomas which gave rise to the supernatants dispensed into these 49 wells produced human antibodies.

(4) Screening of hybridoma producing human IgG type antibody specific to AChR

The culture supernatants of the 49 hybridomas producing human antibodies in the step (3) above were tested for specificity to AChR by the RIA method. A tris buffered solution (pH 7.4), 50 ml in volume, containing the AChR extracted from 25 g of fetal bovine muscle and also containing 2% by volume of α-[4-(1,1,3,3-tetramethylbutyl) phenyl]-ω-hydroxy-poly(oxy-1,2-ethanediyl)] (produced by Sigma Corp, the U.S.A. and marketed under the tradename "Triton X-100") and α-Bungarotoxin labeled with $^{125}I$ possessing a specific activity of about 200 curies/mmol (produced by Amersham & Company, England) were mixed in amounts such as to register a radioactivity concentration of 200 nanocurie/ml. The resultant mixture was shaken at room temperature for about two hours. The mixture consequently obtained was added in a unit volume of 50 μl to 50 μl each of the culture supernatants of the aforementioned hybridomas and left standing overnight at a temperature of 4° C. Portions of the mixture consequently obtained, each combined with 50 μl of a solution prepared by diluting a rabbit anti-human IgG (γ-chain-specific) antiserum (produced by Hoechst, West Germany) with a tris buffered solution (pH 7.4) containing 0.1% by volume of Triton X-100 to twice the original volume, were left standing overnight at a temperature of 4° C. The formed precipitates were each washed three times with a tris buffered solution (pH 7.4) containing 0.1% by volume of Triton X-100 by centrifugation (at the rate of 3,000 rpm for a period of 20 minutes) and were tested for radioactivity with a gamma counter (produced by Aloka K. K. and marketed under the tradename "Autowell Gamma System ARC-361"). The radioactivity data obtained for the precipitates (Sample Nos. 1 to 44) produced by using the culture supernatants of the 44 of a total of 49 hybridomas mentioned above are shown in FIG. 1. For comparison, a precipitate (Sample No. 45) which was produced following the procedure described above, except that the culture supernatant of G(Ag$_1$)$_2$-cl 7B strain was used in the place of the culture supernatant of a hybridoma, was tested for radioactivity. The results are also shown in FIG. 1. As noted from FIG. 1, the precipitate of Sample No. 10 was found to possess high radioactivity. It was therefore concluded that the supernatant which yielded this precipitate possessed a high reactivity to AChR and that the hybridoma which gave rise to this particular supernatant produced a human IgG type antibody specific to AChR.

(5) Cloning of hybridoma

The hybridoma producing the human IgG type antibody specific to AChR, obtained in the step (4) above, was subjected to cloning by the limiting dilution method. This hybridoma was diluted with a RPMI-1640 medium containing about 13% by volume of fetal bovine serum in amounts such as to register concentrations of 50 cells/ml, 10 cells/ml, and 5 cells/ml. The diluted solutions of the concentrations of 50 cells/ml, 10 cells/ml, and 5 cells/ml were each dispensed in a unit volume of 0.1 ml respectively to 40 wells, 32 wells, and 24 wells in a covered 96-well microwell plate made of polystyrene (produced by Nunc Corp., Denmark) and subjected to stationary culture in air containing 7% of carbon dioxide at a temperature of 37° C. After two to four weeks' culture, cell colonies appeared in 17 wells of the plate. The supernatants of each wells which had produced such cell colonies were similarly tested for reactivity to AChR by the RIA method, to screen out one cell line which possessed a high ability to produce a human IgG type monoclonal anti-AChR antibody. This cell line was named as T/G-59(5C) strain.

Figure 2:
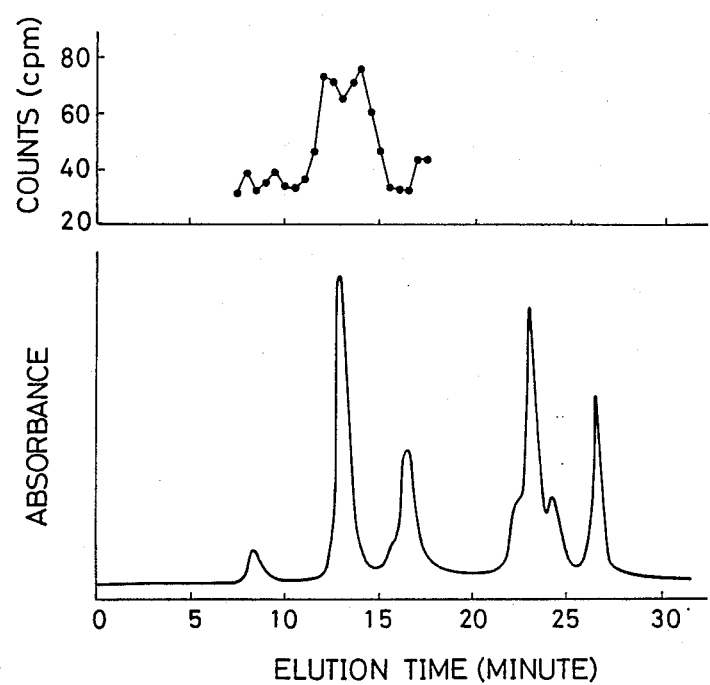
FIG. 2 shows the absorbancy, at a wavelength of 280 nm, of an eluate obtained by subjecting the culture supernatant of the T/G-59(5C) strain to gel permeation chromatography and the value of reactivity to AChR determined by the method of radioimmunoassay using a fraction of the eluate, both in Referential Example 1 (6).

(6) Purification of human IgG type monoclonal anti-AChR antibody produced from T/G-59(5C) strain The T/G-59(5C) strain obtained in the step of (5) above was suspended in a concentration of $1 \times 10^5$ cells/ml in a RPMI-1640 medium containing about 13% by volume of fetal bovine serum and cultured in air containing 7% of carbon dioxide at a temperature of 37° C. At the time that the cell concentration in the culture medium rose over $1 \times 10^6$ cells/ml, the cultured medium was centrifuged for separation of cells. The cells thus obtained were suspended in a concentration of $1 \times 10^5$ cells/ml in a tissue culture-quality serum-free culture medium (produced by Nippon Yakuhin Kaihatsu K. K. and marketed under the tradename "Hybrity-1") and cultured in air containing 7% of carbon dioxide at a temperature of 37° C. At the time that the cell concentration in the culture medium rose over $1 \times 10^6$ cells/ml, the cultured medium was centrifuged to obtain about 1.5 liters of a supernatant. This supernatant was concentrated with an ultrafiltration membrane possessing a fractional molecular weight of 10,000 (produced by Millipore Corp., the U.S.A. and marketed under the tradename "PTGC 043 10"), to obtain about 30 ml of a concentrate. The concentrate was subjected to gel permeation chromatography with a column packed with TSK gel G 3000SW (produced by Toyo Soda Manufacturing Co., Ltd.), using a 0.1 mol/liter sodium acetate buffered solution (pH 5.0) fed as an eluent at a flow rate of 1 ml/min, with the eluate fractionated at intervals of 30 seconds. The fractions were tested for reactivity to AChR by the RIA method in the same manner as in the step of (4). The eluates were tested for absorbance at the wavelength of 280 nm (absorption band specific to protein) and part of the aforementioned fractions were tested for reactivity to AChR. The results are shown in FIG. 2. The fractions occurring within 11.5 to 15.0 minutes' elution time and possessing reactivity to AChR and exhibiting a high absorbance at the wavelength of 280 nm were combined and subjected to affinity chromatography using a carrier (produced by LKB Produkter, Sweden and marketed under the tradename "Blue Triacryl M") for removal of albumin. Part of the human IgG type monoclonal anti-AChR antibody consequently obtained was subjected to electrophoresis using polyacrylamide gel (composed of acrylamide and N,N′-methylene bisacrylamide at a gravimetric ratio of 37:1, having a gel concentration of 8% by weight) in the presence of sodium dodecyl sulfate (used in a concentration of 0.1% by weight). As a result, the human IgG type monoclonal anti-AChR antibody was found to possess a molecular weight of 180,000±20,000. The electrophoretic pattern of this human IgG type monoclonal anti-AChR antibody and that of a commercially available human IgG (produced by Miles Laboratories, the U.S.A. and marketed as Human IgG) are shown in FIG. 3 (1) and FIG. 3 (2) respectively. Based on the comparison of the absorbance, at a wavelength of 280 nm, of the PBS solution containing the human IgG type monoclonal anti-AChR antibody obtained by the aforementioned affinity chromatography and the absorbance at the same wavelength of the PBS solution containing 0.1% by weight of a commercially available human IgG, the amount of the human IgG type monoclonal anti-AChR antibody produced above was found to be about 4.9 mg.

(7) Determination of subclass of human IgG type monoclonal anti-AChR antibody

Figure 4:
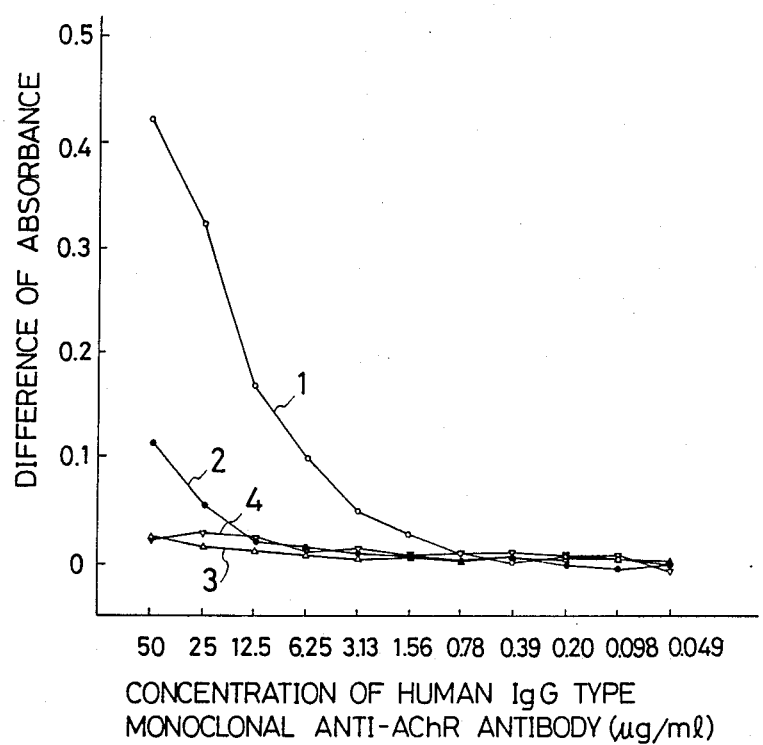
FIG. 4 shows the difference of absorbance at two wavelengths, 409 nm and 501 nm, measured of each of the solutions obtained in the individual wells of a microwell plate by the procedure of coloration in Referential Example 1(7).
Figure 5:
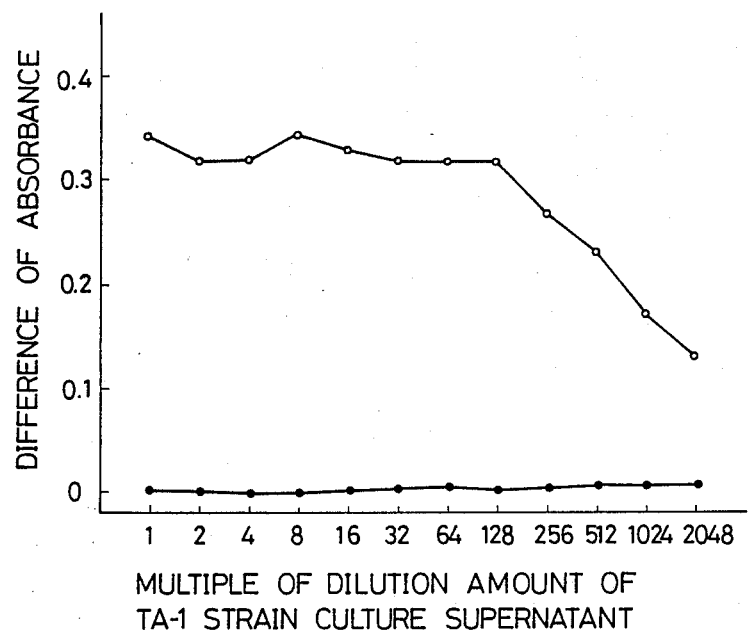
FIG. 5, FIG. 6, FIG. 7 and FIG. 8 severally show the difference of absorbance at the two wavelengths, 409 nm and 501 nm, measured of each of the culture supernatants of strain TA-1, strain TA-2, strain TA-3, and strain TA-5 and the respective diluted solutions.
Figure 6:
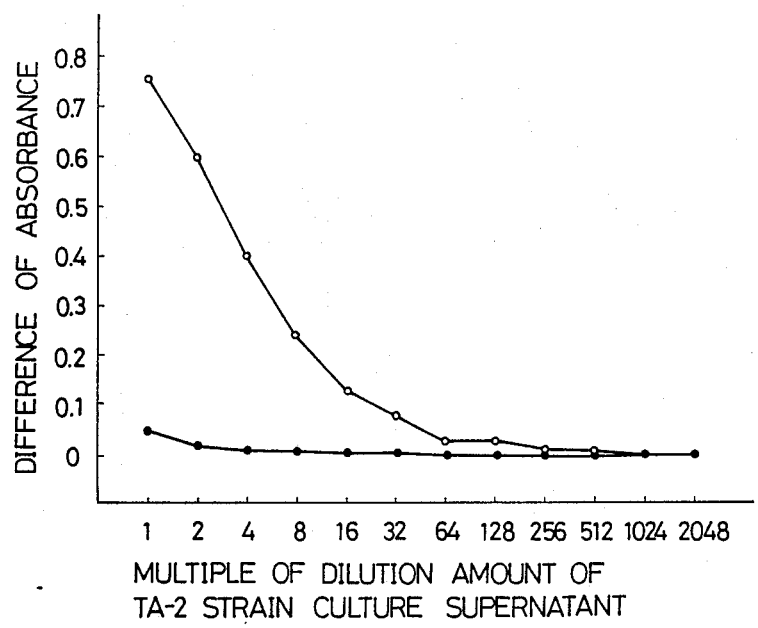
Figure 7:
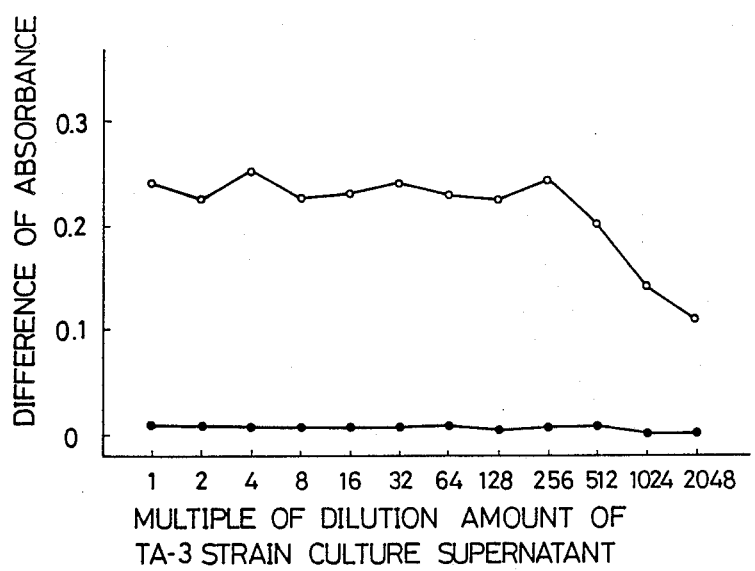
Figure 8:
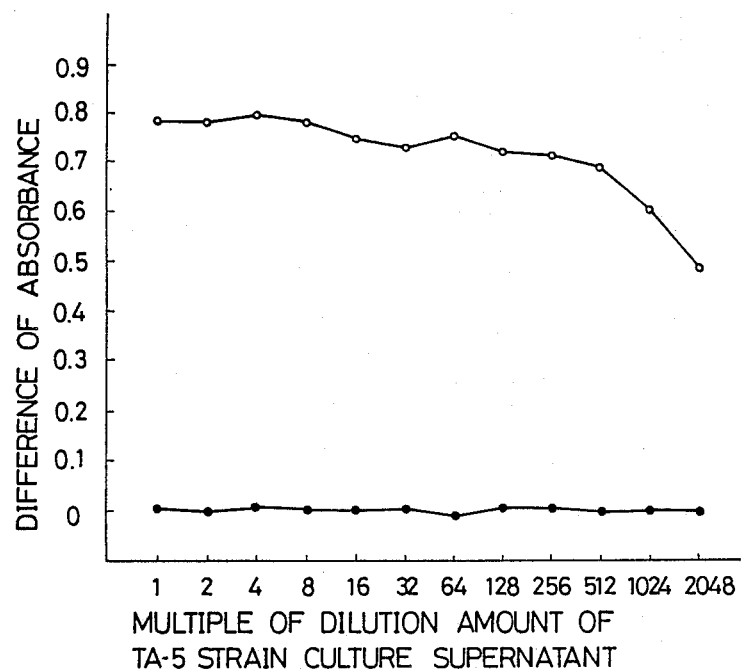

The subclass of the human IgG type monoclonal anti-AChR antibody obtained in the step (6) above was determined by the ELISA method. The human IgG type monoclonal anti-AChR antibody was diluted with PBS to prepare a solution containing the antibody in a concentration of 50 μg/ml. Then by diluting this solution with PBS successively, each twice the former volume, there were obtained 11 solutions of concentrations successively decreased to 0.049 μg/ml. The solution of each of the concentrations was dispensed in a unit volume of 50 μl into four wells of a 96-well microwell plate made of polyvinyl chloride (produced by Becton-Dickinson Corp., the U.S.A. and marketed under the tradename "Falcon 3912") and left standing overnight at a temperature of 4° C., to effect adsorption of a human IgG type monoclonal anti-AChR antibody on the plate. The solutions were removed from the wells. Then, a PBS solution containing 5% by volume of fetal bovine serum was dispensed in a unit volume of 300 μl into the wells and left standing at a temperature of 37° C. for two hours, to effect blocking of the solid-phase surface which had not adsorbed the human IgG type monoclonal anti-AChR antibody and then washed with a PBS solution containing 5% by volume of fetal bovine serum. Mouse monoclonal antibodies against human $IgG_1$, human $IgG_2$, human $IgG_3$, and human $IgG_4$ (produced by Bio-Yeda Corp., Israel and marketed under the tradenames "Monoclonal Anti-human $IgG_1$: Clone SG-11", "Monoclonal Anti-human $IgG_2$: Clone HP-6014", "Monoclonal Anti-human $IgG_3$: Clone HP-6050", and "Monoclonal Anti-human $IgG_4$: Clone HP-25") were each dissolved in a concentration of 5 μg/ml in a PBS solution containing 5% by volume of fetal bovine serum. The four mouse monoclonal antibody solutions consequently obtained were each dispensed in a unit volume of 50 μl into 11 wells having a human IgG type monoclonal anti-AChR antibody adsorbed in differing amounts and left standing at a temperature of 37° C. for one hour. Then, the wells were washed with a PBS solution containing 5% by volume of fetal bovine serum. An anti-mouse immunoglobulin antibody labeled with a horseradishperoxidase (produced by Amersham & Company, England and marketed under the tradename "Anti-mouse Ig, Peroxidaselinked, Species - specific Whole Antibody") was dissolved in a concentration of about 2 μg/ml in a PBS solution containing 5% by volume of fetal bovine serum. The resultant solution was added in a unit volume of 50 μl to each of the wells and left standing at a temperature of 37° C. for one hour. The wells were cleaned with PBS. A tris buffered solution (pH 7.4) containing 2,2′-azino-bis(3-ethylbenzothiazoline-6-sulfonic acid) in a concentration of 1 mmol/liter and also containing 0.0045% by weight of hydrogen peroxide was dispensed in a unit volume of 100 μl to the wells and shaken at room temperature for 15 minutes, to induce coloration. Portions of the solution in the wells were tested for absorbance at wavelengths of 409 nm and 501 nm. The differences of absorbance at the two wavelengths consequently found are shown in a graph of FIG. 4.

In the graph, each curve represents the relation between the concentration of human IgG type monoclonal anti-AChR antibody and the difference of absorbance. Curves 1, 2, 3, and 4 represent the data for the wells into which the mouse monoclonal antibodies against the human $IgG_1$, human $IgG_2$, human $IgG_3$, and human $IgG_4$ had been dispensed. It is clearly noted from FIG. 4 that the human IgG type monoclonal anti-AChR antibody produced by the T/G-59(5C) strain was linked specifically with the mouse anti-human $IgG_1$ monoclonal antibody. Thus, the aforementioned human IgG type monoclonal anti-AChR antibody was concluded to belong to the $IgG_1$ subclass.

EXAMPLE 1

(1) Preparation of spleen cells

An aqueous 0.1 mol/liter sodium acetate buffered solution containing a human $IgG_1$ type monoclonal anti-AChR antibody obtained by the procedure of Referential Example 1 was dialyzed against PBS (pH 7.4). The consequently produced PBS solution containing the human $IgG_1$ type monoclonal anti-AChR antibody was diluted with PBS to prepare a PBS solution containing the human $IgG_1$ type monoclonal anti-AChR antibody in a concentration of 1 mg/ml. This PBS solution was sterilized by filtration. The sterilized PBS solution containing the human $IgG_1$ type monoclonal anti-AChR antibody in a concentration of 1 mg/ml was mixed equivoluminally with Freund's complete adjuvant. A BALB/c mouse was immunized by intraperitoneally injecting a 0.5-ml portion of the resultant emulsion. Three weeks after the immunization, the aforementioned sterilized PBS solution containing the human $IgG_1$ type monoclonal anti-AChR antibody in a concentration of 1 mg/ml was mixed equivoluminally with a suspension of fine aluminum hydroxide precipitates in an aqueous sodium chloride solution (having an aluminum hydroxide content of about 1.2% and a sodium chloride content of 0.15 mol/liter) and a 0.5-ml portion of the resultant mixture was injected intraperitoneally into the aforementioned BALB/c mouse for additional immunization. Three days after the additional immunization, the immunized mouse was sacrificed to excise the spleen. The spleen was pulverized on a stainless steel mesh. From the part of the pulverized spleen which had passed through the mesh, the red blood cells were removed by subjecting this part to a treatment in an aqueous solution containing ammonium chloride and 2-amino-2-hydroxymethyl-1,3-propanediol (tris) in respective concentrations of 0.144 mol/liter and 0.017 mol/liter (pH 7.25). The spleen cells free from the red blood cells were centrifugally cleaned with the RPMI-1640 medium.

(2) Cell fusion

In 1 ml of a mixed solution consisting of 1 g of polyethylene glycol having an average molecular weight of 1,500 and 1 ml of RPMI-1640 medium, $2.5 \times 10^8$ spleen cells obtained in step (1) above and $1.25 \times 10^8$ cells of the P$_3$-NSI/1-Ag$_4$-1 strain were stirred at a temperature of 37° C. for two minutes. To the resultant mixture, 9 ml of the RPMI-1640 medium was gradually added while kept in a stirred state. The mixture consequently obtained was centrifugally separated to obtain a cell mixture as a sediment. To the same HAT culture medium as used in step (2) of Referential Example 1, the cell mixture was added in an amount calculated to account for a final concentration of $1 \times 10^7$ cells/ml. The cell-containing culture medium thus obtained was dispensed in a unit volume of 0.1 ml to 371 wells in four lidded microwell plates of polystyrene (produced by Nunc, Denmark) and subjected to stationary culture in air containing 7% of carbon dioxide at a temperature of 37° C. Growth of hybridoma was recognized in 305 of the aforementioned wells within 10 to 20 days of starting the culture.

(3) Screening of hybridoma producing anti-idiotypic antibody

A PBS solution containing the human IgG$_1$ type monoclonal anti-AChR antibody obtained in Referential Example 1 in a concentration of 0.05 mg/ml was dispensed in a unit volume of 50 μl to the wells of a 96-well microwell plate of polyvinyl chloride (produced by Becton-Dickinson and Company, U.S.A. and marketed under the tradename "Falcon 3912") and was left standing overnight at a temperature of 4° C. to induce adsorption of the antibody on the plate. The individual wells of the plate were emptied of the solution. Then a PBS solution containing 5% by volume of fetal bovine serum was dispensed in a unit volume of 300 μl to the wells and left standing at a temperature of 37° C. for two hours to block the surface of the solid phase which had not adsorbed antibody. The wells were washed with a PBS solution containing 5% by volume of fetal bovine serum. The supernatant of the culture medium in which the propagation of hybridoma was recognized in step (2) above was dispensed in a unit volume of 50 μl to the washed wells and left standing at a temperature of 37° C. for one hour. Then, the wells were washed with a PBS solution containing 5% by volume of fetal bovine serum. An anti-mouse immunoglobulin antibody labeled with horseradish peroxidase (produced by Amersham & Co., England) was dissolved in an approximate concentration of 2 μg/ml in a PBS solution containing 5% by volume of fetal bovine serum. The resultant solution was dispensed in a unit volume of 50 μl to the wells and left standing at a temperature of 37° C. for one hour. Then, the wells were washed with PBS. Then, a tris buffered solution (pH 7.4) containing 2,2'-azino-bis(3-ethylbenzothiazonine-6-sulfonic acid) in a concentration of 1 mmol/liter and hydrogen peroxide in a concentration of 0.0045% by weight was dispensed in a unit volume of 100 μl to the wells and shaken at room temperature for 15 minutes to effect coloration. The solutions formed in the wells were tested for absorbance at wavelengths of 409 nm and 501 nm.

The procedure described above was repeated, except that a commercially available human IgG (produced by Miles Laboratories, U.S.A.) was used in the place of the human IgG$_1$ type monoclonal Anti-AChR antibody obtained in Referential Example 1. The solutions consequently obtained in the wells were tested for absorbance.

As a result of the aforementioned test for absorbance, in the solutions originating in the culture supernatants occurring in 5 of 305 wells which showed recognizable growth of hybridoma in step (2) above, the difference of absorbance at wavelengths 409 nm and 501 nm was large in the solutions obtained by the use of human IgG$_1$ type monoclonal Anti-AChR antibody, whereas substantially no difference of absorbance was recognized at the two wavelengths in the solutions obtained by the use of the commercially available human IgG. Based on the above results, it was concluded that the hybridomas which produced the culture supernatants in the five wells mentioned above yielded anti-idiotypic antibodies specific to the human IgG$_1$ type monoclonal anti-AChR antibody.

(4) Cloning of hybridoma

The hybridomas demonstrated in step (3) above to possess a capacity to produce an anti-idiotypic antibodies specific to the human IgG$_1$ type monoclonal Anti-AChR antibody were subjected to cloning by the limiting dilution method. This cloning was carried out in the same way as in step (5) of Referential Example 1. The culture supernatants in the wells allowing growth of colonies were tested for antibody titer by the same ELISA method as in step (3) above, using the human IgG$_1$ type monoclonal Anti-AChR antibody and the commercially available IgG. Consequently, four cell strains were screened out which exhibited a high capacity to produce a monoclonal anti-idiotypic antibody specific to the human IgG$_1$ type monoclonal anti-AChR antibody. They were labeled respectively as TA-1 strain, TA-2 strain, TA-3 strain, and TA-5 strain.

(5) Determination of subclass of monoclonal anti-idiotypic antibody

The monoclonal anti-idiotypic antibodies produced from the four cell strains obtained in step (4) above were sorted on the level of subclass by the ELISA method. The culture supernatants of the four cell strains were assayed severally by a mouse immunoglobulin test kit (produced by Zymed Corp., U.S.A. and marketed under the tradename "MonoAb-ID EIA Kit"). Consequently the monoclonal anti-idiotypic antibodies produced from these four cell strains were all found to belong to the subclass, IgG$_1$ (κ).

(6) Evaluation of specificity of monoclonal anti-idiotypic antibody

The monoclonal anti-idiotypic antibodies produced from four cell strains obtained in step (4) above were rated with respect to specificity by the ELISA method. First the culture supernatants of the four cell strains were diluted with a PBS solution containing 5% by volume of fetal bovine serum to one half of the original concentration. This dilution was repeated with the same PBS solution at the same ratio of dilution to produce a total of 11 kinds of diluted solutions, so that the last kind of solution had one 2048th of the original concentration. The solutions were tested for antibody titer relative to the human IgG$_1$ type monoclonal Anti-AChR antibody and for antibody titer relative to the commercially available human IgG by the same ELISA method as employed in step (3) above, except that the culture supernatants of the four cell strains and the diluted solutions thereof were used in the place of the culture supernatants of hybridoma. The culture supernatants of strain TA-1 strain, TA-2 strain, TA-3 strain, and TA-5 strain and the solutions obtained by diluting the supernatants were severally tested for absorbance at wavelengths of 409 nm and 501 nm, to obtain data concerning the difference of absorbance at the two wavelengths in each of the diluted solutions. The results are shown in FIG. 5, FIG. 6, FIG. 7, and FIG. 8. In each of the diagrams, the upper curve represents the data obtained for the contents of the wells containing the human IgG$_1$ type monoclonal Anti-AChR antibody and the lower curve those obtained for the contents of the wells containing the commercially available human IgG. From these graphs, it is clearly noted that the monoclonal anti-idiotypic antibodies produced from the four cell strains were all fused specifically with the human IgG$_1$ type monoclonal anti-AChR antibody. From the test results, it was concluded that these monoclonal anti-idiotypic antibodies possessed specificity to the human IgG$_1$ type monoclonal anti-AChR antibody.

(7) Purification of monoclonal anti-idiotypic antibody

The four cell strains obtained in step (4) above were severally suspended in a RPMI-1640 medium containing about 13% by volume of fetal bovine serum in an amount calculated to account for a concentration of $5 \times 10^4$ cells/ml and were cultured in air containing 7% of carbon dioxide at a temperature of 37° C. After the cell concentration in the culture medium increased past $1 \times 10^6$ cells/ml, the cultured medium were centrifuged to obtain respective supernatants. An anti-mouse IgG antibody was obtained by salting out a goat anti-mouse IgG (H+L) antiserum (produced by Bio-Yeda Corp., Israel) with ammonium sulfate. An adsorbent for mouse IgG was prepared by immobilizing this anti-mouse IgG antibody on an agarose type carrier (produced by Pharmacia, Sweden and marketed under the tradename "CNBr-Sepharose CL 4B"). A 100-ml portion of each of the culture supernatants of the aforementioned four cell strains was subjected to affinity chromatography using the mouse IgG adsorbent. By eluting the monoclonal anti-idiotypic antibodies specific to the human IgG$_1$ type monoclonal anti-AChR antibody deposited consequently on the mouse IgG adsorbent with a glycin/hydrochloride buffered solution (pH 2.5), the aforementioned monoclonal anti-idiotypic antibodies were separated each in an amount of about 5 mg. Small portions respectively of the monoclonal anti-idiotypic antibodies produced from the four cell strains were subjected to electrophoresis by the same method as used in step (6) of Referential Example 1 using polyacrylamide gel in the presence of sodium dodecyl sulfate. Consequently, it was found that these monoclonal anti-idiotypic antibodies all had molecular weights falling in the range of 170,000±20,000.

REFERENTIAL EXAMPLE 2

The monoclonal anti-idiotypic antibodies produced from the TA-1 strain, TA-2 strain, TA-3 strain, and TA-5 strain obtained in step (7) of Example 1 were dissolved, each in an amount of about 2 mg, in 2 ml of an aqueous solution containing sodium hydrogen carbonate in a concentration of 0.1 mmol/liter. The resultant solutions were severally mixed with 200 μl of an aqueous dimethylformamide solution containing sulfosuccinimidyl 6-(biotinamide)hexanoate (produced by Pierce Chemical Corp., U.S.A. and marketed under the tradename "NHS-LC-BIOTIN") in a concentration of 1 mg/ml and then left standing at room temperature for four hours. The mixed solutions were dialyzed against PBS solution at a temperature of 4° C. to produce PBS solution containing biotin-labeled monoclonal anti-idiotypic antibodies.

EXAMPLE 2

The serum from a patient of myasthenia gravis was assayed for anti-AChR antibody by the ELISA method using the monoclonal anti-idiotypic antibody produced from the TA-3 strain in step (7) of Example 1 and the biotin-labeled monoclonal anti-idiotypic antibody obtained from the aforementioned monoclonal anti-idiotypic antibody in Referential Example 2 as reagents for detection of anti-AChR antibody.

A PBS solution containing the monoclonal anti-idiotypic antibody produced from the TA-3 strain obtained in step (7) of Example 1 in a concentration of 0.05 mg/ml was dispensed in a unit volume of 50 μl to the wells of a 96-well microwell plate of polystyrene (produced by Becton-Dickinson and Company, U.S.A. and marketed under the tradename "Falcon 3915") and left standing overnight at a temperature of 4° C. to effect adsorption of the monoclonal anti-idiotypic antibodies on the plate. After the wells were emptied of solution, a PBS solution containing 5% by volume of fetal bovine serum was dispensed in a unit volume of 300 μl to the empty wells and left standing at a temperature of 37° C. for two hours, to block the surface of solid phase which had not adsorbed the monoclonal anti-idiotypic antibody. Then, the wells were washed with a PBS solution containing 5% by volume of fetal bovine serum. The sera collected from 20 patients of myasthenia gravis were poured in a unit volume of 50 μl one each in the wells and left standing at 37° C. for two hours. Then, the wells were washed with a PBS solution containing 5% by volume of fetal bovine serum. A PBS solution containing the biotin-labeled monoclonal anti-idiotypic antibody obtained from the monoclonal anti-idiotypic antibody produced from the TA-3 strain in Referential Example 2 and fetal bovine serum in respective concentrations of 4 μg/ml and 5% by volume was prepared using a PBS solution containing the biotin-labeled monoclonal anti-idiotypic antibody. The PBS solution thus obtained was dispensed in a unit volume of 50 μl to the wells and left standing at a temperature of 37° C. for one hour. Then, the wells were washed with a PBS solution containing 5% by volume of fetal bovine serum. Streptavidin labeled with horseradish peroxidase (produced by BRL Corp., U.S.A. marketed under the tradename "Streptavidin-horseradish peroxidase conjugate") was diluted to about 500 times the original weight with a PBS solution containing 5% by volume of fetal bovine serum. The diluted solution was dispensed in a unit volume of 50 μl to the wells and then left standing at a temperature of 37° C. for one hour. Then, the wells were washed with PBS solution. A tris buffered solution (pH 7.4) containing 2,2'-azino-bis(3-ethylbenzothiazoline-6-sulfonic acid) in a concentration of 1 mmol/liter and hydrogen peroxide in a concentration of 0.0045% by weight was dispensed in a unit volume of 100 μl to the wells and shaken at room temperature for 15 minutes to effect coloration.

The procedure described above was repeated, except that PBS solutions containing the human IgG$_1$ type monoclonal anti-AChR antibody obtained in Referential Example 1 in known concentrations in the range of 0.1 ng/ml to 10 μg/ml and also containing fetal bovine serum in a fixed concentration of 5% by volume were used in the place of the sera collected from the patients of myasthenia gravis.

The blood sera and the PBS solutions containing the human $IgG_1$ type monoclonal anti-AChR antibody and the fetal bovine serum were tested for absorbance at wavelengths of 409 nm and 501 nm, to find difference of absorbance at the two wavelength. A standard curve was prepared based on the data of difference of absorbance obtained of the PBS solutions containing the human $IgG_1$ type monoclonal anti-AChR antibody and the fetal bovine serum. The concentrations of anti-AChR antibody in the sera were determined with the aid of this standard curve. As a result, it was confirmed that the concentrations of anti-AChR antibody in the sera collected from the patients of myasthenia gravis all fell in the range of about 10 to 30 ng/ml.

The concentrations of anti-AChR antibody in the sera of the patients of myasthenia gravis were determined by the same ELISA method as described above, except that the monoclonal anti-idiotypic antibodies produced respectively from the TA-1 strain, TA-2 strain, and TA-5 strain and the biotin-labeled monoclonal anti-idiotypic antibodies obtained respectively therefrom were used as reagents for detection of anti-AChR antibody in the place of the monoclonal anti-idiotypic antibody produced from the TA-3 strain and the biotin-labeled monoclonal anti-idiotypic antibodies derived therefrom. The concentrations of anti-AChR antibody in the sera collected from the patients of myasthenia gravis determined by the use of the aforementioned various reagents for detection of anti-AChR antibody were found all to fall in the range of about 10 to 30 ng/ml.

EXAMPLE 3

One (1) g of agarose particles activated with cyanogen bromide (produced by Pharmacia, Sweden and marketed under the tradename "CNBr-Sepharose CL-4B") were washed with an aqueous solution (pH 8.3) containing sodium chloride and sodium hydrogen carbonate in respective concentrations of 0.5 mol/liter and 0.1 mol/liter. The suspension consequently obtained was filtered under suction. The gel consequently obtained was mixed with 10 ml of an aqueous solution (pH 8.3) containing 7 mg of the monoclonal anti-idiotypic antibody produced from the TA-3 strain obtained in the same way as in Example 1 and also containing sodium chloride and sodium hydrogen carbonate in respective concentrations of 0.5 mol/liter and 0.1 mol/liter. The mixture consequently prepared was stirred overnight at a temperature of 4° C. After completion of the stirring, the mixture was filtered under suction. When the filtrate was tested for absorbance at a wavelength of 280 nm, where was found no recognizable absorption due to the monoclonal anti-idiotypic antibody. In 10 ml of a PBS solution containing glycine in a concentration of 1 mol/liter, the gel consequently obtained was stirred overnight at a temperature of 4° C. By washing the mixture with PBS and filtering the washed mixture under suction, there was obtained a gel of agarose particles having 7 mg of the monoclonal anti-idiotypic antibody immobilized thereon.

Gels of agarose particles, each weighing about 3.5 g and having 7 mg of the monoclonal anti-idiotypic antibody, were obtained by following the procedure described above, except that the monoclonal anti-idiotypic antibodies produced from the TA-1 strain, TA-2 strain, and TA-5 strain were used in the place of the monoclonal anti-idiotypic antibody produced from the TA-3 strain.

EXAMPLE 4

In 15 ml of an aqueous solution containing 50% by volume of dioxane, 2.5 ml of epichlorohydrin was stirred. The solution consequently formed was mixed with 10 g of a gel obtained by hydrating cellulose particles (marketed under the tradename "Cellurofine GCL-2000C" by SEIKAGAKU KOGYO CO., LTD.) and 6.5 ml of an aqueous 2N sodium hydroxide solution and the resultant mixture was stirred at a temperature of 40° C. for two hours. The mixture obtained consequently was washed with water and then filtered under suction. The amount, 8.3 g, of the resultant gel was mixed with 16.8 ml of an aqueous solution containing 25 to 28% by weight of ammonia. The resultant mixture was stirred at a temperature of 40° C. for 2.5 hours. The mixture consequently obtained was washed first with water and then with dioxane and filtered under suction, to provide a gel containing dioxane. The amount, 7.53 g, of the gel were mixed with a solution consisting of 1.6 g of succinic anhydride and 24 ml of dioxane and the resultant mixture was stirred overnight at room temperature. The mixture consequently formed was washed with dioxane and filtered under suction. The amount, 7.45 g of the resultant gel was mixed with 0.358 g of N-hydroxysuccinimide, 0.771 g of dicyclohexylcarbodiimide, and 29.8 ml of dioxane. The resultant mixture was stirred overnight at room temperature. The mixture consequently formed was washed first with dioxane and then with a phosphate buffered solution (pH 7.4) of a concentration of 10 mmols/liter and subsequently filtered under suction. The amount, 3.5 g, of the resultant gel was mixed with 7 mg of the monoclonal anti-idiotypic antibody produced from the TA-3 strain by the same method as in Example 1 and 15 ml of a phosphate buffered solution (pH 7.4) of a concentration of 10 mmols/liter. The resultant mixture was stirred overnight at a temperature of 4° C. The mixture consequently formed was filtered under suction. When the filtrate was tested for absorbance at a wavelength of 280 nm, there was found no recognizable absorption due to the monoclonal anti-idiotypic antibody. The gel consequently obtained was washed with PBS and filtered under suction. As a result, there was obtained about 3.5 g of a gel of cellulose particles having 7 mg of the monoclonal anti-idiotypic antibody immobilized thereon.

Gels of cellulose particles, each weighing about 3.5 g and having 7 mg of the monoclonal anti-idiotypic antibody immobilized thereon, were obtained by following the procedure described above, except that the monoclonal anti-idiotypic antibodies produced from the TA-1 strain, TA-2 strain, and TA-5 strain were used in the place of the monoclonal anti-idiotypic antibody produced from the TA-3 strain.

EXAMPLE 5

To 1 ml each of the sera (Nos. 1 to 3) collected from three patients of myasthenia gravis, a gel of agarose particles having immobilized thereon the monoclonal anti-idiotypic antibody produced from the TA-3 strain obtained in Example 3 was added in a unit weight of 50 mg. The resultant mixtures were left standing at a temperature of 37° C. for three hours to effect suspension of the agarose particles therein. The resultant suspensions were centrifuged to produce supernatants. The supernatants thus obtained and the sera before the aforementioned treatment of suspension were assayed by the same ELISA method as in Example 2 to determine their anti-AChR antibody contents. The results are shown in Table 1.

COMPARATIVE EXPERIMENT 1

The procedure of Example 5 was repeated, except that 50 mg of a gel of agarose particles having immobilized thereon a commercially available human IgG (produced by Miles Laboratories Corp., U.S.A. and marketed under the tradename "Human IgG") by the same method as in Example 3 was used in the place of 50 mg of the gel of agarose particles having immobilized thereon the monoclonal anti-idiotypic antibody produced from the TA-3 strain. The supernatants consequently obtained were assayed for anti-AChR antibody concentration. The result are shown in Table 1.

TABLE 1

| Serum No. | Concentration of anti-AChR antibody (ng/ml) | | |
|---|---|---|---|
| | Before treatment | After treatment (Example 5) | After treatment (Comparative Experiment 1) |
| 1 | 16 | 5 | 15 |
| 2 | 26 | 12 | 26 |
| 3 | 20 | 6 | 19 |

EXAMPLE 6

The procedure of Example 5 was repeated, except that gels of agarose particles, each weighing 50 mg and each having immobilized thereon one of the monoclonal anti-idiotypic antibodies produced from the TA-1 strain, TA-2 strain, or TA-5 strain were used in the place of 50 mg of the gels of agarose particles having immobilized therein the monoclonal anti-idiotypic antibody produced from the TA-3 strain. The supernatants obtained after the treatment of suspension were assayed for anti-AChR antibody concentration. As a result, the ratios of removal of anti-AChR antibody from the serum were found all to fall in the range of about 50 to 70%.

EXAMPLE 7

The procedure of Example 5 was repeated, except that gels of agarose particles, each weighing 50 mg and each having immobilized thereon one of the monoclonal anti-idiotypic antibodies produced from the TA-1 strain, TA-2 strain, or TA-5 strain in Example 4 were used in the place of 50 mg of the gels of agarose particles having immobilized therein the monoclonal anti-idiotypic antibody produced from the TA-3 strain. The supernatants obtained after the treatment of suspension were assayed for anti-AChR antibody concentration. As a result, the ratios of removal of anti-AChR antibody from the serum were found all to fall in the range of about 50 to 65%.

As demonstrated by the working examples cited above, this invention permits production of a novel monoclonal anti-idiotypic antibody specific to the human IgG$_1$ type monoclonal anti-AChR antibody with high efficiency owing to the use of a novel hybridoma. The monoclonal anti-idiotypic antibody can be utilized as a reagent for the detection of an anti-AChR antibody and as an adsorbent for the removal of the anti-AChR antibody. The removal of the anti-AChR antibody can be attained by using the adsorbent for the removal of the anti-AChR antibody.

What is claimed is:

1. A monoclonal anti-idiotypic antibody specific to a human IgG$_1$ type monoclonal antibody possessing specificity to a nicotinic acetylcholine receptor, said monoclonal anti-idiotypic antibody being produced by the cells of a strain selected from the group consisting of TA-1 strain (FERM BP-1793), TA-2 strain (FERM BP-1794), TA-3 strain (FERM BP-1795), and TA-5 strain (FERM BP-1796).

2. The monoclonal anti-idiotypic antibody of claim 1, wherein said strain is said TA-1 strain.

3. The monoclonal anti-idiotypic antibody of claim 1, wherein said strain is said TA-2 strain.

4. The monoclonal anti-idiotypic antibody of claim 1, wherein said strain is said TA-3 strain.

5. The monoclonal anti-idiotypic antibody of claim 1, wherein said strain is said TA-5 strain.

6. A cell of a strain selected from the group consisting of TA-1 strain (FERM BP-1793), TA-2 strain (FERM BP-1794), TA-3 strain (FERM BP-1795), or TA-5 strain (FERM BP-1796), said strain being a hybridoma and producing a monoclonal anti-idiotypic antibody specific to a human IgG type monoclonal antibody possessing specificity to a nicotinic acetylcholine receptor.

7. The cell of claim 6, said strain being said TA-1 strain.

8. The cell of claim 6, said strain being said TA-2 strain.

9. The cell of claim 6, said strain being said TA-3 strain.

10. The cell of claim 6, said strain being said TA-5 strain.

11. A method for the detection of an antibody to a nicotinic acetylcholine receptor in a sample, comprising:
  (1) combining said sample with a reagent for the detection of an antibody to a nicotinic acetylcholine receptor, said reagent containing a monoclonal anti-idiotypic antibody specific to a human IgG$_1$ type monoclonal antibody possessing specificity to a nicotinic acetylcholine receptor, said monoclonal anti-idiotypic antibody being produced by the cells of a strain selected from the group consisting of TA-1 strain (FERM BP-1793), TA-2 strain (FERM BP-1794), TA-3 strain (FERM BP-1795), and TA-5 strain (FERM BP-1796); and
  (ii) detecting said antibody to a nicotinic acetylcholine receptor.

12. A method for the removal of an antibody to a nicotinic acetylcholine receptor from a fluid, comprising:
  (i) contacting said fluid with a monoclonal anti-idiotypic antibody specific to a human IgG$_1$ type monoclonal antibody possessing specificity to a nicotinic acetylcholine receptor, said monoclonal anti-idiotypic antibody being produced by the cells of a strain selected from the group consisting of TA-1 strain (FERM BP-1793), TA-2 strain (FERM BP-1794), TA-3 strain (FERM BP-1795), and TA-5 strain (FERM BP-1796) to cause contact between said antibody to a nicotinic acetylcholine receptor and said anti-idiotypic antibody to form a complex; and
  (ii) removing said complex from said fluid.

13. An absorbent for the removal of an antibody to a nicotinic acetylcholine receptor, comprising a monoclonal antibody immobilized onto a particulate carrier, said monoclonal antibody having a monoclonal anti-idiotypic antibody specific to a human IgG$_1$ type monoclonal antibody possessing specificity to the nicotinic acetylcholine receptor, said monoclonal anti-idiotypic antibody being produced by the cells of a strain selected from the group consisting of TA-1 strain (FERM BP-1793), TA-2 strain (FERM BP-1794), TA-3 strain (FERM BP-1795), and TA-5 strain (FERM BP-1796).

14. The absorbent of claim 13, wherein said strain is the TA-1 strain.

15. The absorbent of claim 13, wherein said strain is the TA-2 strain.

16. The absorbent of claim 13, wherein said strain is the TA-3 strain.

17. The absorbent of claim 13, wherein said strain is the TA-5 strain.

* * * * *